US011218734B2

(12) United States Patent
Riehl et al.

(10) Patent No.: US 11,218,734 B2
(45) Date of Patent: Jan. 4, 2022

(54) DATA COMPRESSION IMPLEMENTATION

(71) Applicant: Analog Devices, Inc., Norwood, MA (US)

(72) Inventors: Patrick Riehl, Lynnfield, MA (US); Tony J. Akl, Bedford, MA (US); Venugopal Gopinathan, Boston, MA (US); Hyung Sung Yoon, Lexington, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 0 days.

(21) Appl. No.: 16/787,397

(22) Filed: Feb. 11, 2020

(65) Prior Publication Data

US 2020/0260118 A1    Aug. 13, 2020

Related U.S. Application Data

(60) Provisional application No. 62/804,718, filed on Feb. 12, 2019.

(51) Int. Cl.
| | |
|---|---|
| *H04N 19/65* | (2014.01) |
| *G06N 20/00* | (2019.01) |
| *H04N 19/20* | (2014.01) |
| *H04N 19/91* | (2014.01) |
| *A61B 5/364* | (2021.01) |
| *A61B 5/00* | (2006.01) |

(Continued)

(52) U.S. Cl.
CPC ............ *H04N 19/65* (2014.11); *A61B 5/364* (2021.01); *A61B 5/7232* (2013.01); *G06N 20/00* (2019.01); *H04N 19/20* (2014.11); *H04N 19/91* (2014.11); *A61B 5/318* (2021.01); *A61B 2018/00839* (2013.01); *G06F 1/163* (2013.01)

(58) Field of Classification Search
CPC ........ G06F 1/163; G06N 20/00; H04N 19/20; H04N 19/65; H04N 19/91
See application file for complete search history.

(56) References Cited

U.S. PATENT DOCUMENTS

| | | | | |
|---|---|---|---|---|
| 9,585,621 | B2 * | 3/2017 | Mitov | ................... A61B 5/7203 |
| 2015/0342489 | A1 * | 12/2015 | Bhaumik | ................ A61B 5/352 |
| | | | | 600/521 |
| 2019/0326017 | A1 * | 10/2019 | Goedje | .................. G16H 50/20 |

OTHER PUBLICATIONS

*AZTEC, a Preprocessing Program for Real-Time ECG Rhythm Analysis*, IEEE Transactions on Bio-Medical Engineering, Apr. 1968, 2 pages.

(Continued)

*Primary Examiner* — Joon Kwon
(74) *Attorney, Agent, or Firm* — Patent Capital Group

(57) ABSTRACT

There is disclosed herein examples of systems and methods for compressing a signal. Samples of the signal can be segmented and the samples within each of the segments can be averaged to produce a value that can represent the samples within the segment. The number of samples to average in each segment may be determined based on an error threshold, such that the number of samples being averaged can be maximized to produce less data to be transmitted while maintaining the representation of the samples within the error threshold. In some embodiments, a signal can be separated into a timing reference, a representative periodic function, and a highly compressible error signal. The error signal can be utilized for reproducing a representation of the signal.

22 Claims, 10 Drawing Sheets

(51) Int. Cl.
    *G06F 1/16* (2006.01)
    *A61B 18/00* (2006.01)
    *A61B 5/318* (2021.01)

(56) References Cited

OTHER PUBLICATIONS

Abenstein et al., *A New Data-Reduction Algorithm for Real-Time ECG Analysis*, IEEE Transactions on Biomedical Engineering, vol. BME-29, No. 1, Jan. 1982, 6 pages.

Jalaleddine et al., *ECG Data Compression Techniques—A Unified Approach*, IEEE Transactions on Biomedical Engineering, vol. 37, No. 4, Apr. 1990, 15 pages.

Alam et al., *A DPCM based Electrocardiogram Coder with Thresholding for Real Time Telemonitoring Applications*, International Conference on Communication and Signal Processing, Apr. 3-5, 2014, India, 5 pages.

Gurve et al., *An Improved Lossless ECG Data Compression using ASCII Character Encoding*, IEEE WiSPNET 2016 Conference, 7 pages.

Bera et al., *Real-Time Compression of Electrocardiogram Using Dynamic Bit Allocation Strategy*, 2016 IEEE First International Conference on Control, Measurement and Instrumentation (CMI), 5 pages.

Batista et al., *Compression of ECG Signals Based on Optimum Quantization of Discrete Co-sine Transform Coefficients and Golomb-Rice Coding*, Proceedings of the 25$^{th}$ Annual International Conference of the IEEE EMBS, Cancun, Mexico, Sep. 17-21, 2003, 4 pages.

Pimentel et al., *A FPGA Implementation of a DCT-Based Digital Electrocardiographic Signal Compression Device*, 0-7695-1333-6/01 © 2001 IEEE, 6 pages.

Kim et al., *A Low Power ECG Signal Processor for Ambulatory Arrhythmia Monitoring System*, 2010 Symposium on VLSI Circuits/Technical Digest of Technical Papers, 2 pages.

Deepu et al., *An ECG-SoC with 535nW/Channel Lossless Data Compression for Wearable Sensors*, 978-1-4799-0280-4/13 © 2013 IEEE, 4 pages.

Chen et al., *VLSI Architecture of lossless ECG Compression Design based on Fuzzy Decision and Optimization Method for Wearable Devices*, Electronics Letters, 3$^{rd}$ Sep. 2015, vol. 51, No. 18, 2 pages.

Ieong et al., *A 0.45 V 147-375 nW ECG Compression Processor with Wavelet Shrinkage and Adaptive Temporal Decimation Architectures*, IEEE Transactions on Very Large Scale Integration (VLSI) Systems, vol. 25, No. 4, Apr. 2017, 13 pages.

Fira et al. *An ECG Signals Compression Method and Its Validation Using NNs*, IEEE Transactions on Biomedical Engineering, vol. 55, No. 4, Apr. 2008, 8 pages.

Ding et al., *ECG Compression for Mobile Sensor Platforms*, 978-1-5090-3087-3 © 2016 IEEE, 6 pages.

Mamaghanian et al., *Compressed Sensing for Real-Time Energy-Efficient ECG Compression on Wireless Body Sensor Nodes*, IEEE Transactions on Biomedical Engineering, vol. 58, No. 9, Sep. 2011, 11 pages.

Zou et al., *An Energy-Efficient Design for ECG Recording and R-Peak Detection Based on Wavelet Transform*, IEEE Transactions on Circuits and Systems—II: Express Briefs, vol. 62, No. 2, Feb. 2015, 5 pages.

\* cited by examiner

DATA COMPRESSION IMPLEMENTATION

RELATED APPLICATIONS

The present disclosure claims priority to U.S. provisional application No. 62/804,718 entitled "DATA COMPRESSION IMPLEMENTATION" and filed Feb. 12, 2019, the disclosure of which is incorporated by reference in its entirety.

FIELD OF THE DISCLOSURE

This disclosure relates in general to the field of data compression, and more particularly, though not exclusively, to systems and methods of data compression for wearable monitors.

BACKGROUND

With the advent of mobile devices and the limited supply of power from the battery of the mobile devices, providing power-efficient wireless communication of data has been prevented as a challenge. In particular, transmission of data via a transmitter of a mobile device can drain the power from the battery. Some legacy approaches to reduce the power drain of wireless communication include generating compressed signals representing an original signal, where the compressed signals could be transmitted while drawing less power than transmission of the original signal. However, the legacy approaches struggle with providing inadequate representations of the original signal due to the compression and/or lacking optimization of the compression leading to lack of optimization of the power draw.

BRIEF DESCRIPTION OF THE DRAWINGS

The present disclosure is best understood from the following detailed description when read with the accompanying figures. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion.

EMBODIMENTS OF THE DISCLOSURE

Figure 1:
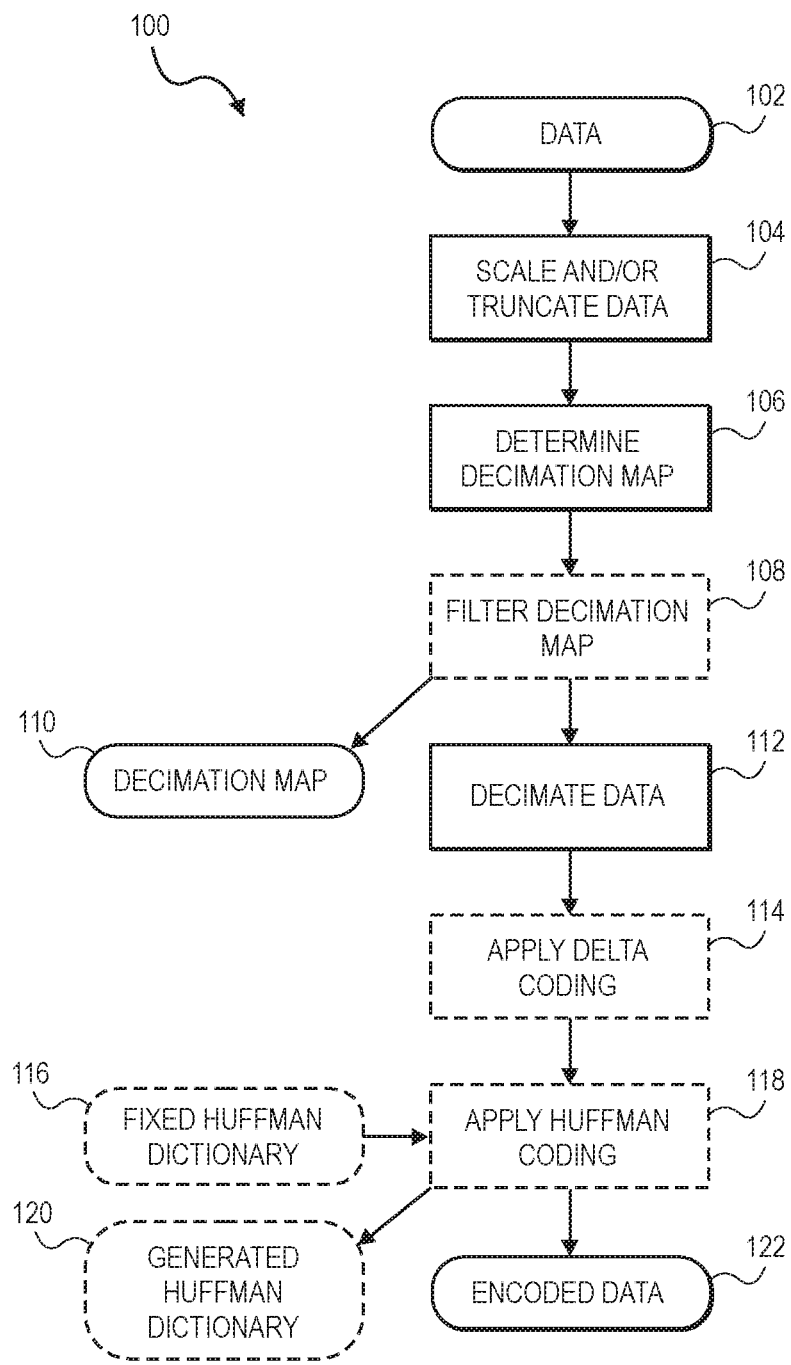
FIG. 1 illustrates an example data encode procedure, according to embodiments of the present disclosure.

The following disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples, or in some cases across different figures. This repetition is for the purpose of simplicity and clarity and does not in itself dictate a specific relationship between the various embodiments and/or configurations discussed. Different embodiments may have different advantages, and no particular advantage is necessarily required of any embodiment.

FIG. 1 illustrates an example data encode procedure 100, according to embodiments of the present disclosure. The data encode procedure 100 may be performed by a microprocessor or other circuitry. In some embodiments, computer-readable media may store instructions that, when executed by the microprocessor or another device, cause the microprocessor or the device to perform the data encode procedure 100. Further, the data encode procedure 100 may be performed by a mobile data collection device (such as an electrocardiogram (ECG) monitor) that performs the data encode procedure 100 on data captured by the data collection device prior to transmitting (either wirelessly or wiredly) encoded data representing the captured data to a remote device.

In stage 102 of the data encode procedure 100, data may be received by the entity performing the data encode procedure 100. The data may comprise an analog signal, a digital signal, samples captured from an analog or digital signal, or some combination thereof. For example, the data may comprise an analog signal detected by an ECG sensor.

In stage 104, the entity may scale and/or truncate the data. For example, the entity may discard bits below a predetermined noise level. Discarding the bits may minimize the number of delta codes applied in stage 114. In some embodiments where an analog signal is received in stage 102, stage 104 may further include sampling the analog signal to produce a plurality of samples representing the analog signal. For example, the entity may sample the analog signal at a set frequency where a sample value of the analog signal is produced each time the entity samples the analog signal.

In stage 106, the entity may determine a decimation map for the data. Determination of the decimation map is described further in relation to FIG. 2.

In stage 108, the entity may filter the decimation map. In particular, the entity may identify low energy outlier segments within the data and absorb the outlier segments into a neighboring high-energy cluster. In some embodiments, stage 108 may be omitted.

In stage 110, a decimation map may be produced by the entity. The decimation map may be produced based on the determination of the decimation map and/or the filtering of the decimation map performed in stage 106 and stage 108, respectively. In some embodiments, the decimation map may be compressed for transmission. For example, the entity may apply run-length encoding to the decimation map to compress the decimation map. The entity may transmit, or provide for transmission of, the decimation map to a remote device, where the remote device may utilize the decimation map to produce a representation of the data received in stage 102. The decimation map transmitted to the remote device may be compressed in some embodiments and may not be compressed in other embodiments.

In stage 112, the entity may decimate the data. In particular, the entity may decimate the data in accordance with the decimation map produced in stage 110. The decimation of the data is described further in FIG. 2.

In stage 114, the entity may apply delta coding to the decimated data. For example, the entity may take a first difference of the data to reduce a number of codes. In some embodiments, stage 114 may be omitted.

In stage 116, a fixed Huffman dictionary may be received for encoding of the decimated data by the entity. In some embodiments, stage 116 may be omitted.

In stage 118, the entity may apply Huffman coding to the decimated data. In some embodiments, the entity may apply the Huffman coding to the decimated signal after delta coding has been applied to the decimated data. For example, the entity may encode the most common values within the decimated data with shorter codes.

In stage 120, the entity may produce a Huffman dictionary. The Huffman dictionary may be based on the decimated data and may comprise a data-driven Huffman dictionary. In some embodiments, the produced Huffman dictionary may be based from the fixed Huffman dictionary received in stage 116.

In stage 122, the entity may produce encoded data that represents the data received in stage 102. The encoded data may have been produced via the decimation, delta coding, and/or Huffman coding performed in stage 112, stage 114, and stage 118, respectively.

Figure 2:
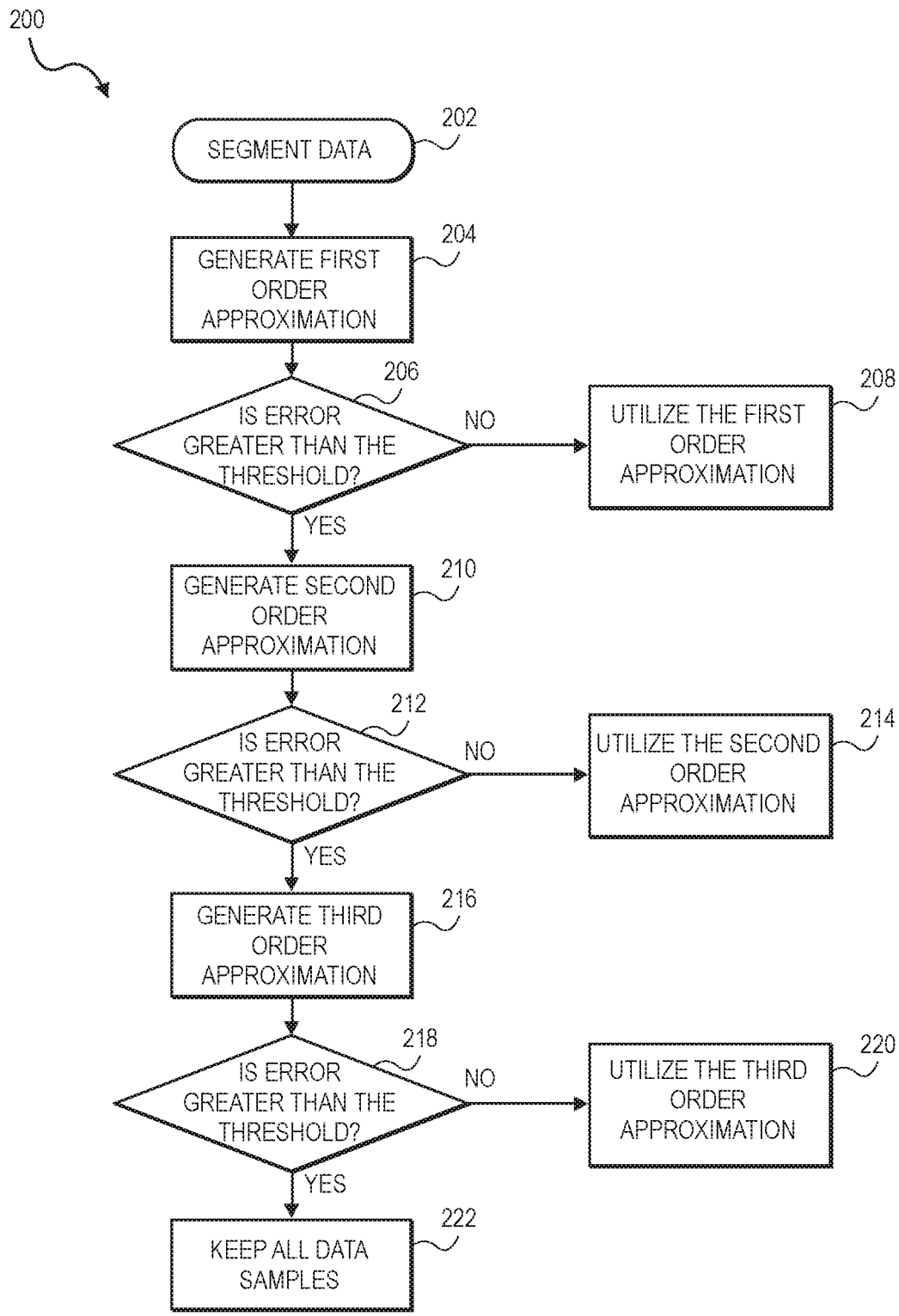
FIG. 2 illustrates an example decimation determination procedure, according to embodiments of the present disclosure.

FIG. 2 illustrates an example decimation determination procedure 200, according to embodiments of the present disclosure. The decimation determination procedure 200 may be performed as part of stage 106, stage 108, stage 110, and/or stage 112 of FIG. 1. In particular, the decimation determination procedure 200 may be utilized for determination of the decimation map, production of the decimation map, and/or performing decimation of the data. FIG. 3A through FIG. 3F illustrate graphical representations of the example decimation determination procedure 200 of FIG. 2, according to embodiments of the present disclosure.

In stage 202, an entity may identify a data segment to be decimated. The data segment may include a segment of data received by the entity to be decimated or an entirety of data received by the entity to be decimated. For example, the data segment may include a segment of the data received by the entity in stage 102 (FIG. 1) or may include an entirety of the data received by the entity in stage 102. The data samples included in the data segment may be identified by the entity based on a certain feature of the data samples, such as the data samples exceeding a certain value, a sign of the value of the data samples, a certain portion of a signal represented by the data samples, or some combination thereof.

In stage 204, the entity may generate a first order approximation of the data samples within the data segment. Generating the first order approximation may include determining a number of data samples to be averaged to produce the approximation or may include determining a number of approximation segments to be made of the data samples. The number of data samples or the number of approximation segments for the first order approximation may be selected to produce a minimized number of approximation segments. For example, the number of data samples or the number of approximation segments for the first order approximation may be selected to produce one approximation segment in some embodiments. For each sample within the data segment, the entity may produce a corresponding sample in the approximation segments.

Figure 3A:
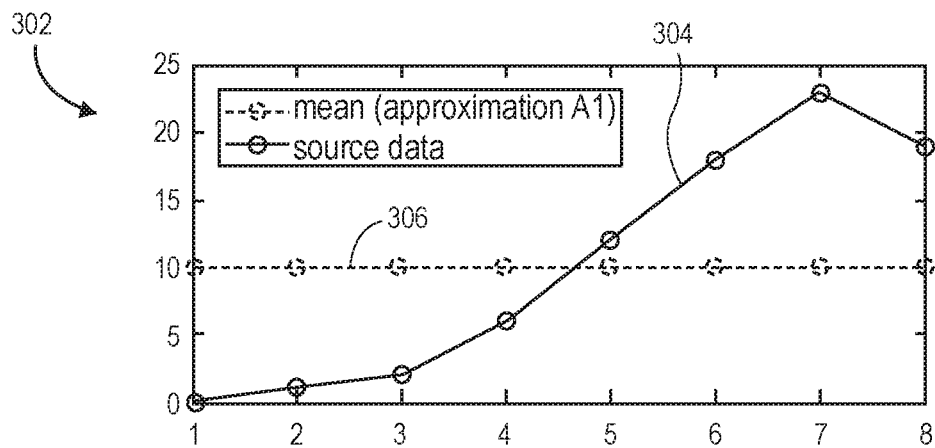
FIG. 3A illustrates a graphical representation of a first approximation of the example decimation determination procedure of FIG. 2, according to embodiments of the present disclosure.

FIG. 3A illustrates a graphical representation of a first approximation of the example decimation determination procedure of FIG. 2, according to embodiments of the present disclosure. In particular, chart 302 illustrates an example representation of a first order approximation of a data segment 304. The data segment 304 may include eight samples. In some embodiments, the data segment 304 may represent a portion of an ECG signal. The first order approximation may include a single approximation segment generated from the eight samples. The entity may determine a mean of the eight samples and set the value of the eight corresponding samples of the approximation segment 306 to the mean of the eight samples.

In stage 206, the entity may determine whether an error of the first order approximation is greater than an error threshold. In particular, the entity may compare the samples of the first order approximation with the corresponding samples of the data segment to determine whether the difference between each of the samples of the first order approximation and the samples of the data segment exceed the error threshold. The error threshold may be a percentage, a magnitude, or some combination thereof. The error threshold may be the same for each data segment received by the entity or may vary among different data segments received by the entity. Further, the error threshold may be predetermined, may be determined based on the data segment, or may be programmable by a user of the entity. For example, the error threshold for each data segment may be determined based on the feature utilized for determining to include the samples in the data segment. The entity may utilize the maximum absolute error value, the root-mean-squared error value, or any other suitable metric, for determining whether the error is greater than the error threshold. If the error of the first order approximation is less than the error threshold, the decimation determination procedure 200 may proceed to stage 208. If the error of the first order approximation is greater than the error threshold, the decimation determination procedure 200 may proceed to stage 210.

Figure 3B:
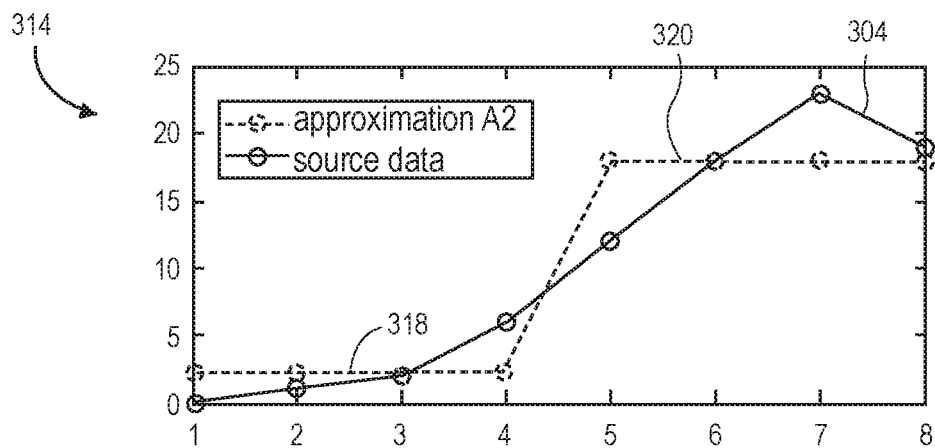
FIG. 3B illustrates a graphical representation of a second approximation of the example decimation determination procedure of FIG. 2, according to embodiments of the present disclosure.
Figure 3C:
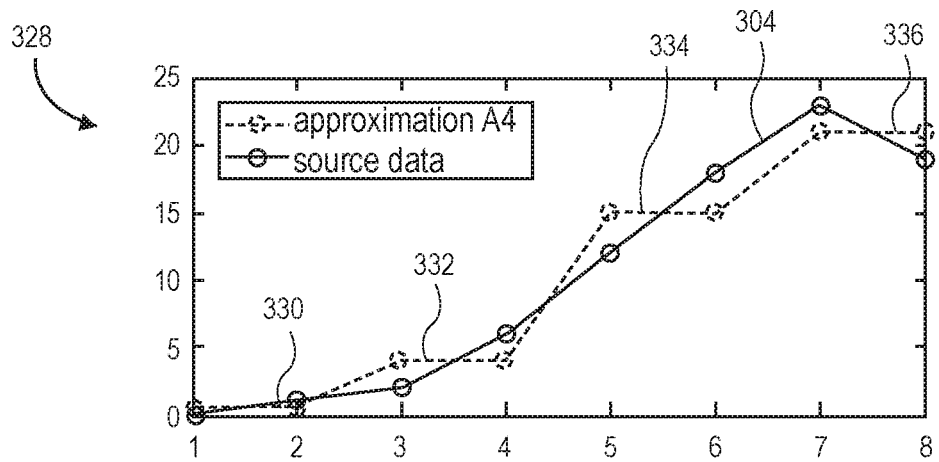
FIG. 3C illustrates a graphical representation of a third approximation of the example decimation determination procedure of FIG. 2, according to embodiments of the present disclosure.
Figure 3D:
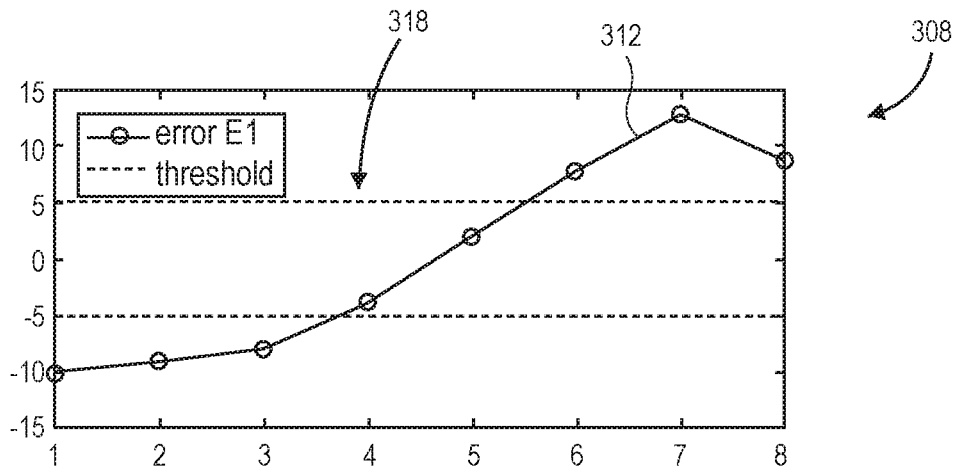
FIG. 3D illustrates a graphical representation of an error determination of the first approximation of the example decimation determination procedure of FIG. 2, according to embodiments of the present disclosure.

FIG. 3D illustrates a graphical representation of an error determination of the first approximation of the example decimation determination procedure of FIG. 2, according to embodiments of the present disclosure. In particular, chart 308 illustrates an example representation of the determination of whether the maximum absolute value error of the first order approximation is greater than the error threshold. In the illustrated embodiment, the error threshold is set to a value of 5. The entity may produce an error threshold envelope 310 from −5 to 5. The entity may further produce an error amount line 312 by determining the difference between each of the samples of the approximation segment 306 and the corresponding samples of the data segment 304. The entity may then determine whether the error amount line 312 is within the error threshold envelope 310, thereby determining whether the error of the first order approximation is greater than the error threshold.

In stage 208, the entity may determine that the first order approximation is to be utilized based on the error of the first order approximation being less than the error threshold. For example, the entity may utilize the first order approximation for stage 106, stage 108, stage 110, and stage 112 of the data encode procedure 100 (FIG. 1). The decimation determination procedure 200 may be exited at stage 208.

In stage 210, the entity may generate a second order approximation of the data samples within the data segment. Generating the second order approximation may include determining a number of data samples to be averaged to produce the approximation or may include determining a number of approximation segments to be made of the data samples. The number of data samples or the number of approximation segments for the second order approximation may be selected to produce more approximation segments than the first order approximation. For example, the number of data samples or the number of approximation segments for the second order approximation may be selected to produce two approximation segments in some embodiments. For each sample within the data segment, the entity may produce a corresponding sample in the approximation segments.

FIG. 3B illustrates a graphical representation of a second approximation of the example decimation determination procedure of FIG. 2, according to embodiments of the present disclosure. In particular, chart 314 illustrates an example representation of a second order approximation of the data segment 304. The second order approximation may include two approximation segments. In particular, the second order approximation may include a first approximation segment 318 generated from the first four samples of the data segment 304 and a second approximation segment 320 generated from the last four samples of the data segment 304. The entity may determine a mean of the first four samples and set the value of the four corresponding samples of the first approximation segment 318 to the mean of the first four samples. Further, the entity may determine a mean of the last four samples and set the value of the four corresponding samples of the second approximation segment 320 to the mean of the last four samples.

In stage 212, the entity may determine whether an error of the second order approximation is greater than the error threshold. In particular, the entity may compare the samples of the second order approximation with the corresponding samples of the data segment to determine whether the difference between each of the samples of the second order approximation and the samples of the data segment exceed the error threshold. The entity may utilize the maximum absolute error value, the root-mean-squared error value, or any other suitable metric, for determining whether the error is greater than the error threshold. If the error of the second order approximation is less than the error threshold, the decimation determination procedure 200 may proceed to stage 214. If the error of the second order approximation is greater than the error threshold, the decimation determination procedure 200 may proceed to stage 216.

Figure 3E:
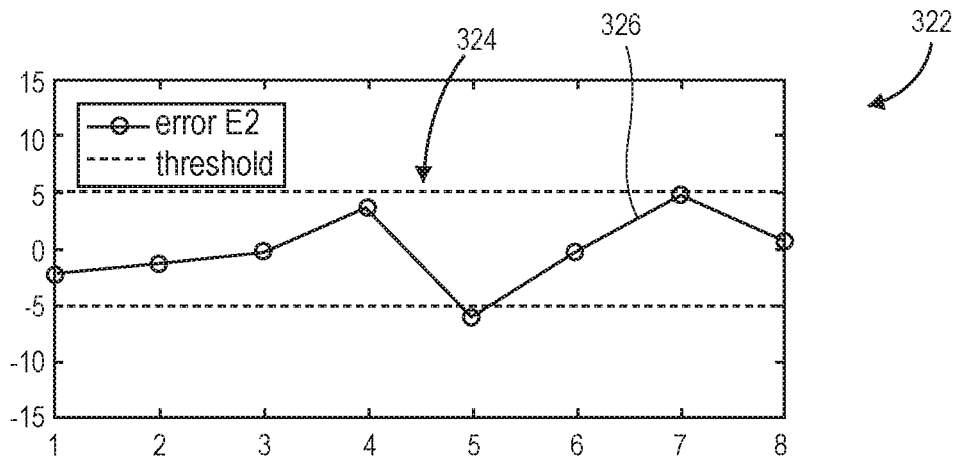
FIG. 3E illustrates a graphical representation of an error determination of the second approximation of the example decimation determination procedure of FIG. 2, according to embodiments of the present disclosure.

FIG. 3E illustrates a graphical representation of an error determination of the second approximation of the example decimation determination procedure of FIG. 2, according to embodiments of the present disclosure. In particular, chart 322 illustrates an example representation of the determination of whether the error of the second order approximation is greater than the error threshold. In the illustrated embodiment, the error threshold is set to a value of 5. The entity may produce an error threshold envelope 324 from −5 to 5. The entity may further produce an error amount line 326 by determining the difference between each of the samples of the first approximation segment 318 and the corresponding samples of the data segment 304, and between each of the samples of the second approximation segment 320 and the corresponding samples of the data segment 304. The entity may then determine whether the error amount line 326 is within the error threshold envelope 324, thereby determining whether the error of the first order approximation is greater than the error threshold.

In stage 214, the entity may determine that the second order approximation is to be utilized based on the error of the second order approximation being less than the error threshold. For example, the entity may utilize the second order approximation for stage 106, stage 108, stage 110, and stage 112 of the data encode procedure 100 (FIG. 1). The decimation determination procedure 200 may be exited at stage 214.

In stage 216, the entity may generate a third order approximation of the data samples within the data segment. Generating the third order approximation may include determining a number of data samples to be averaged to produce the approximation or may include determining a number of approximation segments to be made of the data samples. The number of data samples or the number of approximation segments for the third order approximation may be selected to produce more approximation segments than the second order approximation. For example, the number of data samples or the number of approximation segments for the third order approximation may be selected to produce four approximation segments in some embodiments. For each sample within the data segment, the entity may produce a corresponding sample in the approximation segments.

FIG. 3C illustrates a graphical representation of a third approximation of the example decimation determination procedure of FIG. 2, according to embodiments of the present disclosure. In particular, chart 328 illustrates an example representation of a third order approximation of the data segment 304. The third order approximation may include four approximation segments. In particular, the third order approximation may include a first approximation segment 330 generated from the first two samples of the data segment 304, a second approximation segment 332 generated from the next two samples of the data segment 304, a third approximation segment 334 generated from the next two samples of the data segment 304, and a fourth approximation segment 336 generated from the last two samples of the data segment 304. The entity may determine a mean of the first two samples and set the value of the two corresponding samples of the first approximation segment 330 to the mean of the first two samples. The entity may determine a mean of the next two samples and set the value of the two corresponding samples of the second approximation segment 332 to the mean of the two samples. The entity may determine a mean of the next two samples and set the value of the two corresponding samples of the third approximation segment 334 to the mean of the two samples. The entity may determine a mean of the last two samples and set the value of the two corresponding samples of the fourth approximation segment 336 to the mean of the two samples.

In stage 218, the entity may determine whether an error of the third order approximation is greater than the error threshold. In particular, the entity may compare the samples of the third order approximation with the corresponding samples of the data segment to determine whether the difference between each of the samples of the third order approximation and the samples of the data segment exceed the error threshold. The entity may utilize the maximum absolute error value, the root-mean-squared error value, or any other suitable metric, for determining whether the error is greater than the error threshold. If the error of the third order approximation is less than the error threshold, the decimation determination procedure 200 may proceed to stage 220. If the error of the third order approximation is greater than the error threshold, the decimation determination procedure 200 may proceed to stage 222.

Figure 3F:
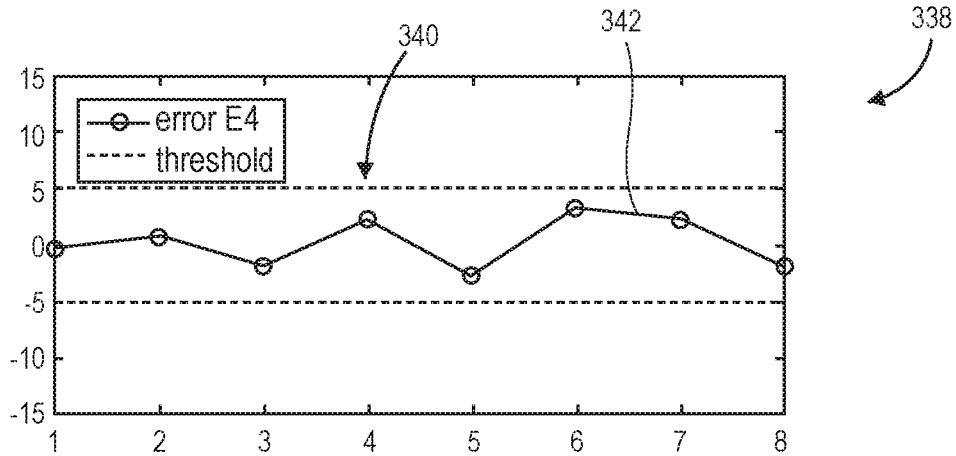
FIG. 3F illustrates a graphical representation of an error determination of the third approximation of the example decimation determination procedure of FIG. 2, according to embodiments of the present disclosure.

FIG. 3F illustrates a graphical representation of an error determination of the third approximation of the example decimation determination procedure of FIG. 2, according to embodiments of the present disclosure. Chart 338 illustrates an example representation of the determination of whether the error of the third order approximation is greater than the error threshold. In the illustrated embodiment, the error threshold is set to a value of 5. The entity may produce an error threshold envelope 340 from −5 to 5. The entity may further produce an error amount line 342 by determining the difference between each of the samples of the first approximation segment 330 and the corresponding samples of the data segment 304, between each of the samples of the second approximation segment 332 and the corresponding samples of the data segment 304, between each of the samples of the third approximation segment 334 and the corresponding samples of the data segment 304, and between each of the samples of the fourth approximation segment 336 and the corresponding samples of the data segment 304. The entity may then determine whether the error amount line 342 is within the error threshold envelope 340, thereby determining whether the error of the third order approximation is greater than the error threshold.

In stage 220, the entity may determine that the third order approximation is to be utilized based on the error of the third order approximation being less than the error threshold. For example, the entity may utilize the third order approximation for stage 106, stage 108, stage 110, and stage 112 of the data encode procedure 100 (FIG. 1). The decimation determination procedure 200 may be exited at stage 220.

In stage 222, the entity may have determined that the approximations may not be performed while the error threshold is satisfied. In this case, the entity may utilize all the data samples of the data segment. For example, the entity may utilize all the data samples for stage 106, stage 108, and stage 112 of the data encode procedure 100. The decimation determination procedure 200 may be exited at stage 222.

While three orders of approximation are described in relation to the decimation determination procedure 200, it is to be understood that the decimation determination procedure 200 may include greater or fewer orders of approximation in other embodiments. Further, the amount of segments for each of the orders of approximation are examples and the amount of segments may differ in other embodiments.

The decimation determination procedure 200 may be repeated for each data segment to be decimated, where the error threshold may be different for different data segments. In some embodiments, the entity may limit a change in the order of approximation for decimation between consecutive segments of the data received by the entity. For example, the data received by the entity may comprise a signal, where the difference between the order of approximation utilized for decimation of consecutive portions of the signal may be limited to be below a threshold difference. As an example, if a first segment of the data is determined to be decimated using a second order approximation and the threshold difference is one order, the order of approximation for decimation of the subsequent segment of the data may be limited to within one order of the first segment, which can be a first order approximation, a second order approximation, or a third order approximation being determined for decimation of the subsequent segment. Limiting the change in the order of approximation for decimation between consecutive segments of data may reduce artifacts in a reconstructed signal.

One or more decimation maps may be produced based on the decimation determination procedure 200. The decimation maps may indicate the order of approximation that has been determined for decimating the samples and the decimation that has been performed on the samples. The decimation maps may be utilized to create a representation of the signal based on the results of the decimation of the samples.

Figure 4:
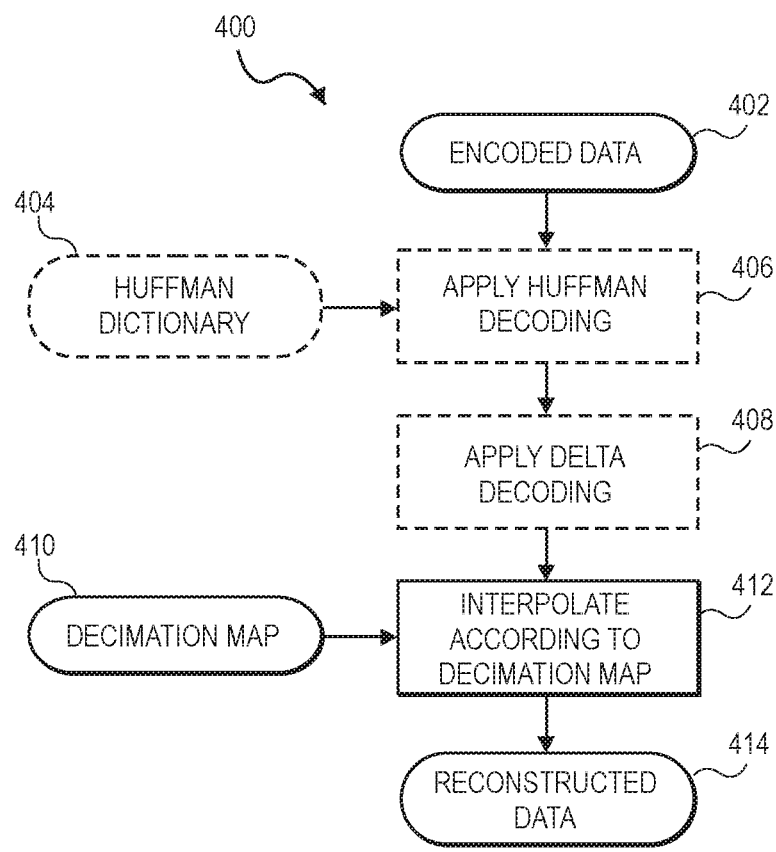
FIG. 4 illustrates an example data decode procedure, according to embodiments of the present disclosure.

FIG. 4 illustrates an example data decode procedure 400, according to embodiments of the present disclosure. The data decode procedure 400 may be performed by a device remote from the entity that performs the data encode procedure 100 (FIG. 1). For example, an ECG monitor may perform the data encode procedure 100 and a data server separate from the ECG monitor may perform the data decode procedure 400 in some embodiments.

In stage 402, the device may receive encoded data. In particular, the device may receive the encoded data produced by the entity in stage 122 (FIG. 1). The device may receive the encoded data wirelessly or wiredly from the entity.

In stage 404, the device may receive or access a Huffman dictionary. For example, the Huffman dictionary may be a fixed Huffman dictionary (such as the fixed Huffman dictionary referenced in stage 116 (FIG. 1)), and the device may access the fixed Huffman dictionary from memory of the device or receive the fixed Huffman dictionary from the entity in some embodiments. In other embodiments, the entity may produce a Huffman dictionary (such as the Huffman dictionary referenced in stage 120 (FIG. 1)) and provide the Huffman dictionary to the device.

In stage 406, the device may apply Huffman decoding to the encoded data. In particular, the device may utilize the Huffman dictionary received or accessed in stage 404 to apply Huffman decoding to the encoded data. In some embodiments, stage 404 and stage 406 may be omitted. For example, when Huffman coding was not utilized to generate the encoded data received in stage 402, stage 404 and stage 406 may be omitted.

In stage 408, the device may apply delta decoding to the encoded data. In some embodiments, stage 408 may be omitted. For example, when delta coding was not utilized to generate the encoded data received in stage 402, stage 408 may be omitted.

In stage 410, the device may receive a decimation map. The decimation map may be a decimation map produced by the entity while generating the encoded data. For example, the device may receive the decimation map produced in stage 110 (FIG. 1).

In stage 412, the device interpolates according to the decimation map. For example, device may utilize samples of the encoded data received in stage 402 and the decimation map to create reconstructed data.

In stage 414, the device produces reconstructed data. The reconstructed data may be based on the interpolation according to the decimation map performed in stage 412. The reconstructed data may include a signal, such as an analog signal or a digital signal.

Figure 5:
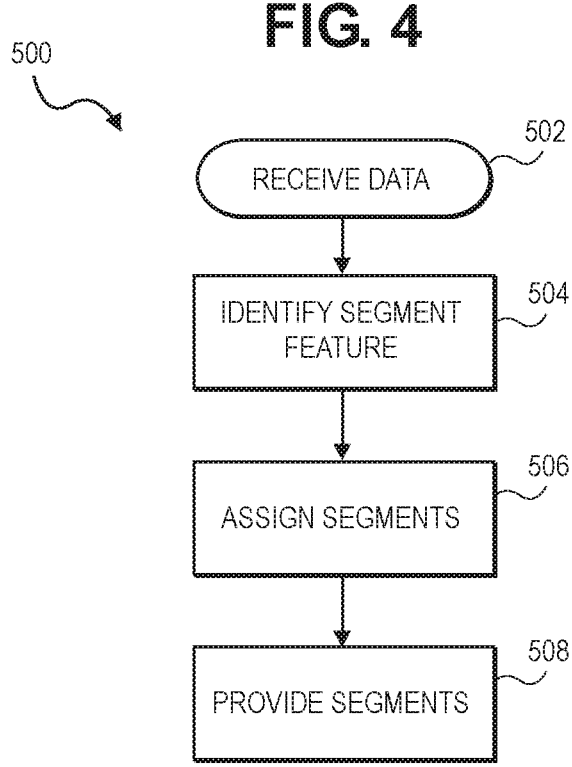
FIG. 5 illustrates an example segment determination procedure, according to embodiments of the present disclosure.
Figure 6:
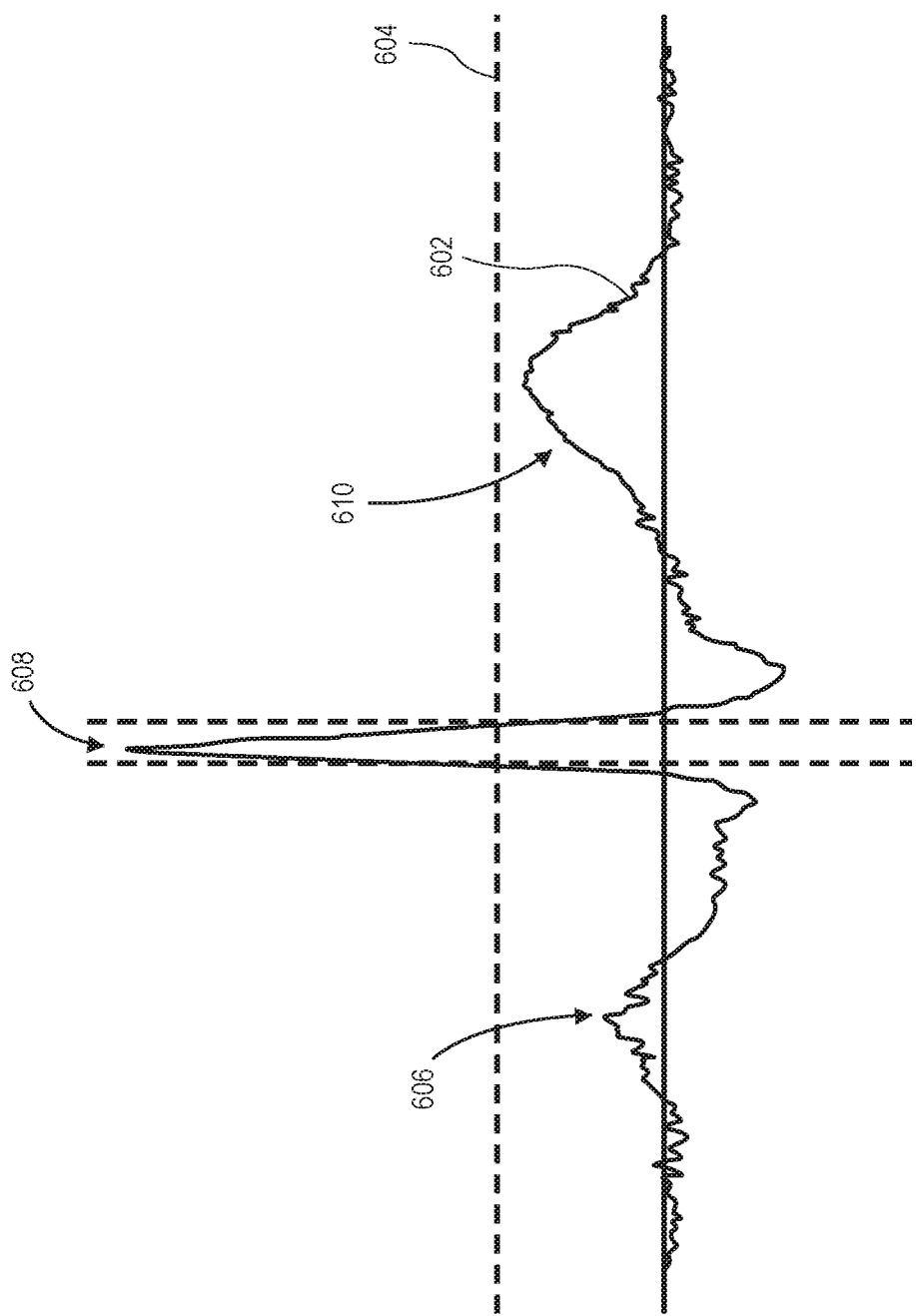
FIG. 6 illustrates a graphical representation of the example segment determination procedure of FIG. 5, according to embodiments of the present disclosure.

FIG. 5 illustrates an example segment determination procedure 500, according to embodiments of the present disclosure. The segment determination procedure 500 may be performed by the entity that performs the data encode procedure 100. FIG. 6 illustrates a graphical representation of the example segment determination procedure 500 of FIG. 5, according to embodiments of the present disclosure.

In stage 502, the entity may receive data. The data may include a signal (such as an analog or a digital signal) or samples of a signal. In some embodiments, the signal may be an ECG signal. FIG. 6 illustrates a signal 602 that may be received by the entity.

In stage 504, the entity may identify one or more occurrences of segmentation features. The segmentation features may comprise any characteristic of the received data that may be utilized by the entity for determining segments of the data. For example, the segmentation features may include certain voltage ranges that indicate which segment a portion of the data is to be assigned, a certain voltage that indicates a new segment of the data is to be assigned, a certain time range that indicates which segment a portion of the data is to be assigned, a certain time that indicates a new segment of the data is to be assigned, or some combination thereof. In some embodiments, the segmentation features may indicate that portions of the data that exceed a certain magnitude are to be assigned to certain segments, while portions of the data below the certain magnitude are to be assigned to other segments. Line 604 of FIG. 6 illustrates a magnitude segmentation feature, where portions of the signal 602 with magnitudes greater than the line 604 are to be assigned to certain portions and portions of the signal 602 with magnitudes less than the line 604 are to be assigned to other portions.

In stage 506, the entity assigns segments to the data. In particular, the entity assigns segments to the data based on the segmentation features. FIG. 6 illustrates results of assigning the segments based on the magnitude segmentation feature indicated by the line 604. The entity may assign a first segment 606 to a first portion of the signal 602 based on the magnitude of the first portion being less than the magnitude indicated by the line 604. The entity may assign a second segment 608 to a second portion of the signal 602 based on the magnitude of the second portion being greater than the magnitude indicated by the line 604. Further, the entity may assign a third segment 610 to a third portion of the signal 602 based on the magnitude of the third portion being less than the magnitude indicated by the line 604 and being separate from the first portion.

In stage 508, the entity may provide the segments. Providing the segments may comprise sequentially providing each of the segments or indications of the assignments of the segments. The segments may be utilized by the data encode procedure 100 for allowing the encoding to be performed on each segment to be determined individually. For example, the entity may determine that a certain decimation map may be utilized for one of the segments and a different decimation map may be utilized for another of the segments. Further, each of the segments may be individually provided in stage 102 for performance of the data encode procedure 100, or all segments may be provided in stage 102 and then may be processed individually.

Figure 7:
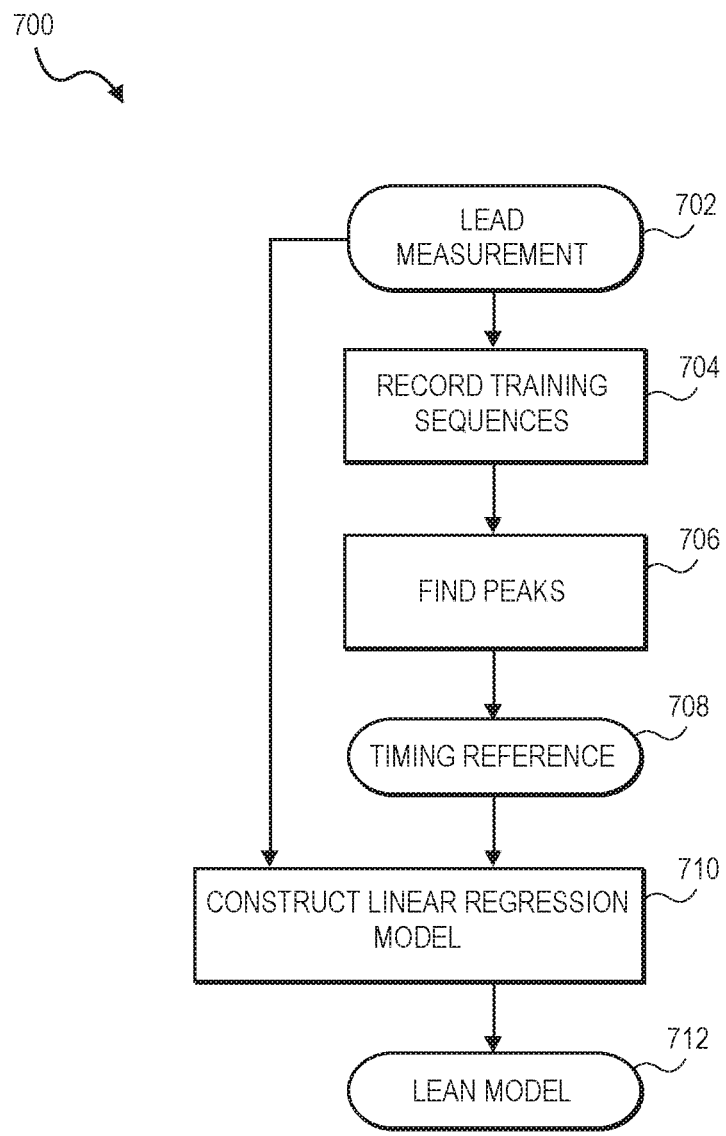
FIG. 7 illustrates an example training procedure, according to embodiments of the present disclosure.

In some instances, a signal of interest, such as an ECG, may be largely periodic in the sense that most of the useful information contained in the signal can be expressed by a model comprising first, a detailed pattern representing a single period of the signal, and second, a timing reference that indicates the rate at which that pattern repeats. In such cases, the residual signal representing the difference between the model and the actual signal may be utilized to reconstruct the complete signal. However, this residual signal may contain few features of interest and thus, it may be highly compressible. Accordingly, a compression approach may comprise of a training procedure 700 followed by a compression procedure 800. FIG. 7 illustrates an example training procedure 700, according to embodiments of the present disclosure. In some embodiments, the entity may perform the training procedure 700 to take advantage of signals that are periodic. The training procedure 700 may be performed by the same entity that performs the data encode procedure 100 (FIG. 1).

In stage 702, the entity may receive one or more lead measurements from a sensor. The lead measurement may comprise a signal, and, in some embodiments, may comprise an ECG signal. The sensor may comprise one or more electrodes to capture the signal. In some instances, the electrodes may be placed on the skin of a subject and capture the signal from the subject.

In stage 704, the entity may record the signal received via the measurement as one or more training sequences. A training sequence may include one or more repetitions of the signal, which is periodic. The training sequences may be stored in memory.

In stage 706, the entity may find peaks of each the repetitions of the signal within the training sequences. For example, the training sequences may be retrieved from memory and peaks may be found in the training sequences. The peaks may be all the peaks within the repetitions, a certain portion of the peaks within the repetitions, a peak with the greatest magnitude within each of the repetitions, a peak with the greatest positive magnitude within each of the repetitions, a peak with the greatest negative magnitude within each of the repetitions, or some combination thereof. In some embodiments, the peak may be an R peak of an ECG signal, where the R peak may be due to depolarization of the ventricular Myocardium.

In stage 708, the entity may generate a timing reference. In some embodiments, the timing reference may be a 1-bit timing reference that may be utilized to indicate the timing of the peaks identified in stage 706.

In stage 710, the entity may construct a linear regression model of the training sequences. The entity may construct the linear regression model based on the lead measurement, the identified peaks, and the timing reference.

In stage 712, the entity may provide the linear regression model as a lead model. The lead model may be utilized to reconstruct a signal. For example, the lead model may comprise a base for a signal, where a timing reference (such as the timing reference produced in stage 806 (FIG. 8)) when used with the lead model may produce a signal.

Figure 8:
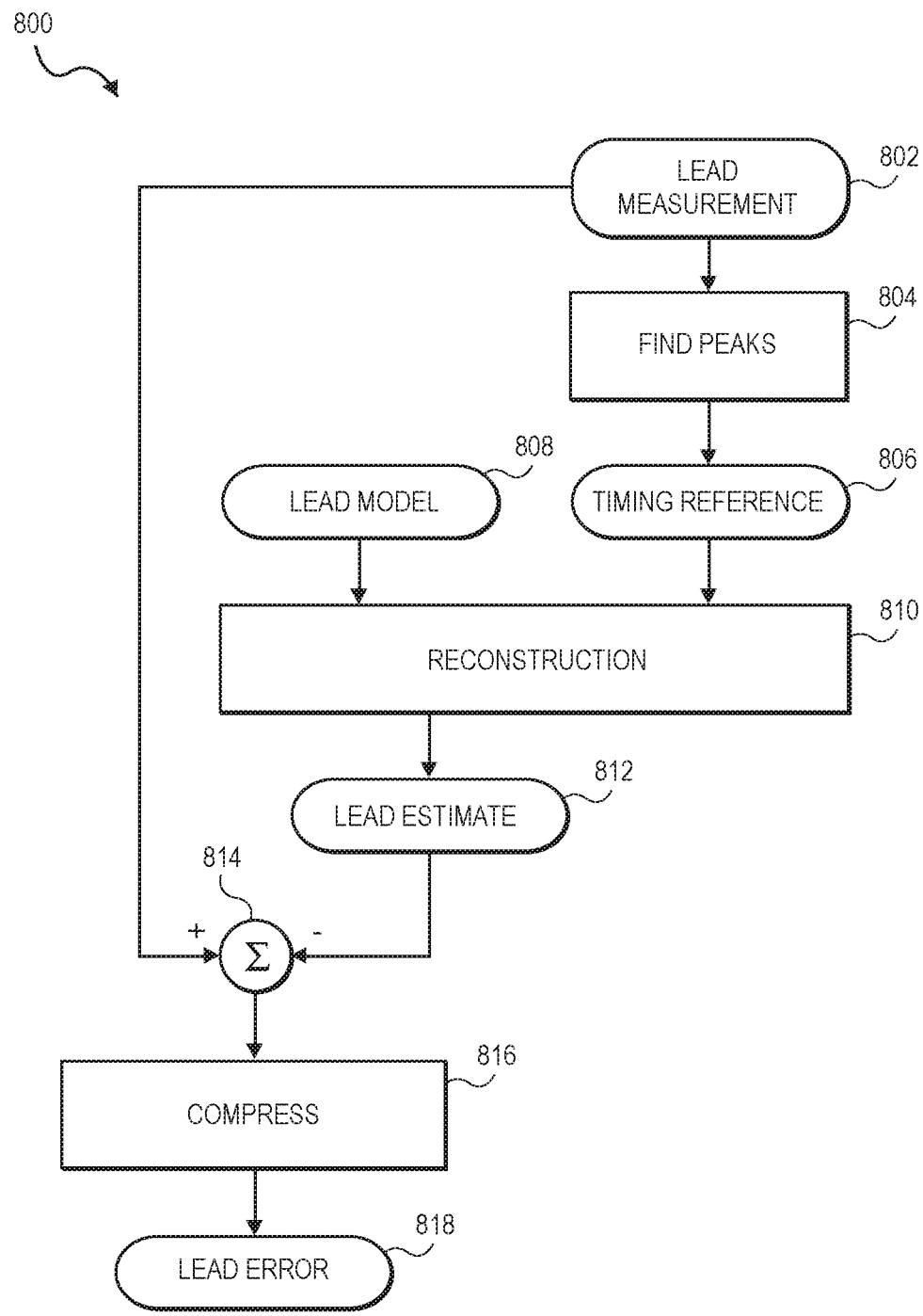
FIG. 8 illustrates an example compression procedure, according to embodiments of the present disclosure.

FIG. 8 illustrates an example compression procedure 800, according to embodiments of the present disclosure. The compression procedure 800 may be performed by the same entity that performs the data encode procedure 100 (FIG. 1) and the training procedure 700 (FIG. 7).

In stage 802, the entity may receive one or more lead measurements from a sensor. The lead measurement may comprise a signal, and, in some embodiments, may comprise an ECG signal. The sensor may comprise one or more electrodes to capture the signal. In some instances, the electrodes may be placed on the skin of a subject and capture the signal from the subject. The lead measurements may be stored in a memory.

In stage 804, the entity may find peaks of the lead measurements. For example, the lead measurements may be retrieved from memory and the peaks may be found in the lead measurements. The peaks may be all the peaks within the lead measurement, a certain portion of the peaks within the lead measurement, a peak with the greatest magnitude within the lead measurement, a peak with the greatest positive magnitude within the lead measurement, a peak with the greatest negative magnitude within the lead measurement, or some combination thereof. In some embodiments, the peak may be an R peak of an ECG signal, where the R peak may be due to depolarization of the ventricular Myocardium.

In stage 806, the entity may produce a timing reference. In some embodiments, the timing reference may be a 1-bit timing reference.

In stage 808, the entity may receive and/or access a lead model. The lead model may be the lead model provided by the training procedure 700 in stage 712. The lead model may comprise a base for a signal, where a timing reference (such as the timing reference produced in stage 806) when used with the lead model may produce a signal.

In stage 810, the entity may perform reconstruction of an estimate of the lead measurement. The entity may reconstruct the estimate based on the lead model and the timing reference. The estimate of the lead measurement may comprise an estimate of the signal of the lead measurement. The reconstruction with the lead model and the timing reference may produce a signal that estimates the signal of the lead measurement from stage 802.

In stage 812, the entity may produce a lead estimate. The lead estimate may be produced by the reconstruction performed in stage 810. The lead model may comprise an estimated signal that estimates the signal of the lead measurement from stage 802.

In stage 814, the entity may sum the lead measurement received in stage 802 and the lead estimate produced in stage 812. In particular, the entity may sum the positive value of the lead measurement received in stage 802 with the negative value of the lead estimate to determine a difference between the lead measurement and the lead estimate.

In stage 816, the entity may compress the results of the summation performed in stage 814 using any suitable compression approach, such as the data encode procedure 100 (FIG. 1). The results of the compression may comprise an error between the lead measurement and the lead estimate.

In stage 818, the entity may produce a lead error. The lead error may be a compressed representation of the difference between the lead measurement received in stage 802 and the lead estimate produced in stage 812. The lead error may be utilized to produce a signal that represents the signal of the lead measurement. For example, the lead error may be utilized with a lead model (such as the lead model produced in stage 712 (FIG. 7)) to produce a signal that estimates the signal of the lead measurement. The lead error may be highly compressible based on the information represented by the lead error.

Figure 9:
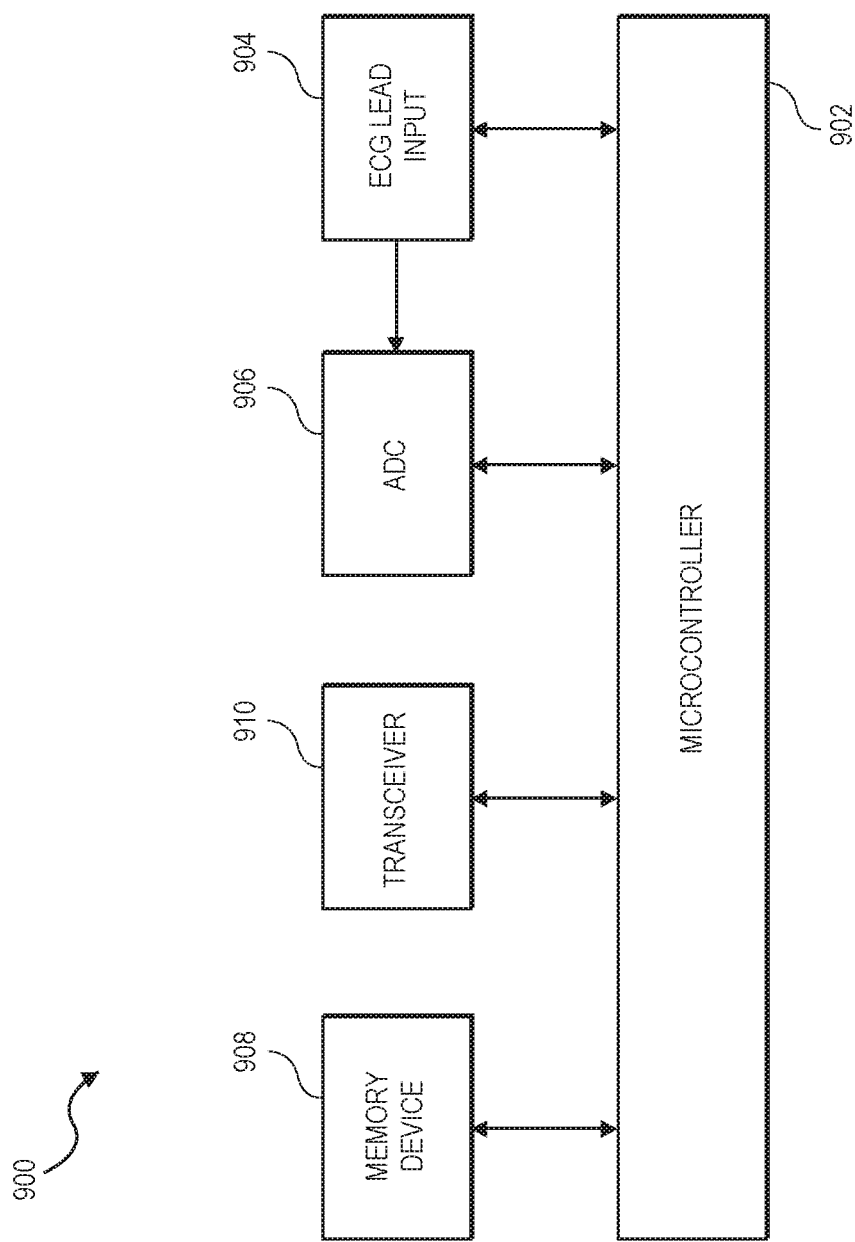
FIG. 9 illustrates example circuitry of a device, according to embodiments of the present disclosure.

FIG. 9 illustrates example circuitry 900 of a device, according to embodiments of the present disclosure. The device may comprise an ECG monitor, where the circuitry 900 may comprise a portion of the circuitry of the ECG monitor. The circuitry 900, or some portion thereof, may perform one or more of the procedures described herein, including the data encode procedure 100 (FIG. 1), the decimation determination procedure 200 (FIG. 2), the segment determination procedure 500 (FIG. 5), training procedure 700 (FIG. 7), and/or the compression procedure 800 (FIG. 8). In some embodiments, a microcontroller 902 of the circuitry 900 may perform the procedures described herein.

The circuitry 900 may include an ECG lead input 904. The ECG lead input 904 may be coupled to an ECG lead that is to be applied to a subject and produce a signal that represents the electrical activity of a heart of the subject. The ECG lead input 904 may receive the signal produced by the ECG lead.

The circuitry 900 may further include an analog-to-digital converter (ADC) 906. The ADC 906 may be coupled to the ECG lead input 904 and may receive the signal from the ECG lead input 904, where the signal is received in analog format. The ADC 906 may produce a digital format representation of the of the signal. For example, the ADC 906 may sample the signal in analog format and may produce a plurality of samples of the signal that may be utilized in the data encode procedure 100, the decimation determination procedure 200, the segment determination procedure 500, the training procedure 700, and/or the compression procedure 800. In other embodiments, the ADC 906 may be omitted from the circuitry 900 and the microcontroller 902 may perform the analog-to-digital conversion.

The circuitry 900 may further include the microcontroller 902. The microcontroller 902 may comprise one or more processors, such as one or more microprocessors. The microcontroller 902 may be coupled to the ADC 906 and/or the ECG lead input 904, and may receive the output from the ADC 906 or the output of the ECG lead input 904. The microcontroller 902 may perform one or more of the operations described herein with the data received from the ADC 906 or the ECG lead input 904. In some embodiments, the entity described throughout this disclosure may refer to the microcontroller 902.

The circuitry 900 may further include one or more memory devices 908. The memory devices 908 may be coupled to the microcontroller 902. The memory devices 908 may comprise computer-readable memory devices that may store instructions that, when executed by the microcontroller 902, cause the microcontroller 902 to perform one or more of the operations described herein. Further, the microcontroller 902 may utilize the memory devices 908 to store data, such as the results of the operation performed by the microcontroller 902 on the data received from the ADC 906 or the ECG lead input 904.

The circuitry 900 may further include a transceiver 910. In some embodiments, the transceiver 910 may comprise low energy Bluetooth circuitry and an antenna. In other embodiments, the transceiver 910 may comprise any components that facilitate wireless and/or wired data links, such as universal serial bus (USB) circuitry. The microcontroller 902 may utilize the transceiver 910 to transmit data to a remote device. For example, the microcontroller 902 may provide data to the transceiver 910, where the transceiver 910 may convert the data for transmission.

Figure 10:
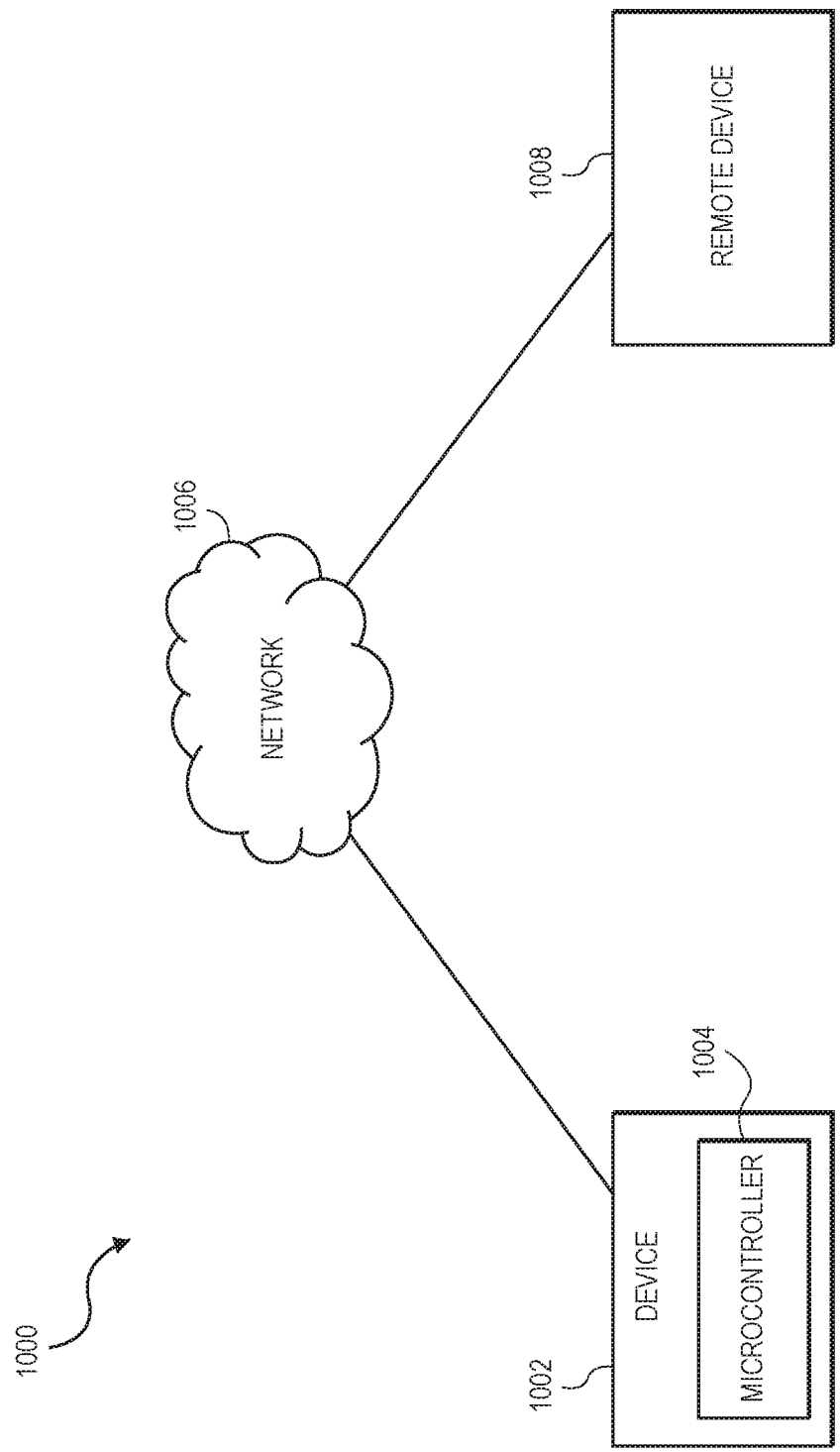
FIG. 10 illustrates an example arrangement, according to embodiments of the present disclosure.

FIG. 10 illustrates an example arrangement 1000, according to embodiments of the present disclosure. The arrangement 1000 may implement the entity described herein.

The arrangement 1000 may include a device 1002. The device 1002 may be a monitoring device in some embodiments. For example, the device 1002 may comprise a monitoring device, such as an ECG monitor. The device 1002 may include a microcontroller 1004, which may perform and/or control one or more of the operations performed by the device 1002. In some embodiments, the device 1002 may implement the circuitry 900 (FIG. 9), where the microcontroller 1004 may comprise the microcontroller 902 (FIG. 9) of the circuitry 900. The entity described throughout this disclosure may refer to the device 1002 in some embodiments or to the microcontroller 1004 in other embodiments. The device 1002, or some portion thereof, may perform one or more of the operations of the entity described herein, including the data encode procedure 100 (FIG. 1), the decimation determination procedure 200 (FIG. 2), the segment determination procedure 500 (FIG. 5), the training procedure 700 (FIG. 7), and/or the compression procedure 800 (FIG. 8).

The arrangement 1000 may further include a network 1006. The network 1006 may be coupled to multiple devices and may provide for wireless communication among the devices. For example, the network 1006 may be coupled to the device 1002 and may provide for wireless communication with the device 1002. In some embodiments, the network 1006 may comprise a Bluetooth network.

The arrangement 1000 may further include a remote device 1008. The remote device 1008 may comprise a computer device that is separate from the device 1002. The remote device 1008 may be coupled to the network 1006 and may exchange data with the device 1002 via the network 1006. In some embodiments, the remote device 1008 may perform the data decode procedure 400. Further, the remote device 1008 may comprise an intermediary device that facilitates communication between the device 1002 and another remote device (such as a server) via the network 1006 or another network. In other embodiments, the remote device 1008 may comprise a server that can exchange data with the device 1002 and analyze the data received from the device.

EXAMPLE IMPLEMENTATIONS

The following examples are provided by way of illustration.

Example 1 may include a device, comprising a memory device to store samples of a signal, and a microcontroller coupled to the memory device, the microcontroller to assign a first portion of the samples to a first segment based on a segmentation feature of the first portion of the samples, assign a second portion of the samples to a second segment based on a segmentation feature of the second portion of the samples, perform decimation of the first segment, wherein the decimation of the first segment utilizes a first segment order approximation for the decimation of the first segment, and perform decimation of the second segment, wherein the decimation of the second segment utilizes a second segment order approximation for the decimation of the second segment.

Example 2 may include the device of example 1, wherein the segmentation feature of the first portion of the samples comprises values of the first portion of the samples exceeding a certain magnitude, and wherein the segmentation feature of the second portion of the samples comprises values of the second portion of the samples being below the certain magnitude.

Example 3 may include the device of example 1, wherein the first segment order approximation is determined based on an average of the first portion of the samples and a first error threshold for the first segment, and wherein the second segment order approximation is determined based on an average of the second portion of the samples and a second error threshold for the second segment.

Example 4 may include the device of example 3, wherein the first error threshold is determined based on the segmentation feature of the first portion of the samples, and wherein the second error threshold is determined based on the segmentation feature of the second portion of the samples.

Example 5 may include the device of example 4, wherein the first error threshold and the second error threshold are different.

Example 6 may include the device of example 1, wherein the first segment order approximation is of a different order from the second segment order approximation.

Example 7 may include the device of example 1, wherein the microcontroller is further to generate one or more approximations of the first segment, compare one or more values of the one or more approximations of the first segment with values of the first portion of the samples to determine amounts of error for the one or more approximations of the first segment, compare the amounts of error for the one or more approximations of the first segment with a first error threshold, wherein an order of the first segment order approximation is determined based on the comparison of the amounts of error for the one or more approximations of the first segment with the first error threshold, generate one or more approximations of the second segment, compare one or more values of the one or more approximations of the second segment with values of the second portion of the samples to determine amounts of error for the one or more approximations of the second segment, and compare the amounts of error for the one or more approximations of the second segment with a second error threshold, wherein an order of the second segment order approximation is determined based on the comparison of the amounts of error for the one or more approximations of the second segment with the second error threshold.

Example 8 may include the device of example 1, wherein to perform the decimation of the first segment includes to produce a first decimation map for the first segment based on the first segment order approximation, wherein the first decimation map is utilized for the decimation of the first segment, and to perform the decimation of the second segment includes to produce a second decimation map for the second segment based on the second segment order approximation, wherein the second decimation map is utilized for the decimation of the second segment.

Example 9 may include the device of example 8, wherein the microcontroller is further to provide a result of the decimation of the first segment to a remote device, provide the first decimation map to the remote device, provide a result of the decimation of the second segment to the remote device, and provide the second decimation map to the remote device, wherein the remote device is to utilize the first decimation map with the first segment and the second decimation map with the second segment to produce a representation of the signal.

Example 10 may include one or more computer-readable media having instructions stored thereon, wherein the instructions, when executed by a device, cause the device to identify a first portion of samples of a signal, the first portion of the samples identified based on a first segmentation feature common to the first portion of the samples, identify a second portion of the samples, the second portion of the samples identified based on a second segmentation feature common to the second portion of the samples, determine a first decimation map for the first portion of the samples based on an approximation of the first portion of the samples and a first error threshold for the first portion of the samples, and determine a second decimation map for the second portion of the samples based on an approximation of the second portion of the samples and a second error threshold for the second portion of the samples.

Example 11 may include the one or more computer-readable media of example 10, wherein to determine the first decimation map includes to generate one or more approximations of the first portion of the samples, wherein each of the one or more approximations of the first portion is of different order, and compare values of the one or more approximations of the first portion of the samples with the first portion of the samples to determine which of the one or more approximations of the first portion of the samples are within the first error threshold, wherein the approximation of the first portion of the samples utilized for determination of the first decimation map is included in the one or more approximations of the first portion of the samples that are within the first error threshold, and to determine the second decimation map includes to generate one or more approximations of the second portion of the samples, wherein each of the one or more approximations of the second portion is of different order, and compare values of the one or more approximations of the second portion of the samples with the second portion of the samples to determine which of the one or more approximations of the second portion of the samples are within the second error threshold, wherein the approximation of the second portion of the samples utilized for determination of the second decimation map is included in the one or more approximations of the second portion of the samples that are within the second error threshold.

Example 12 may include the one or more computer-readable media of example 10, wherein the first segmentation feature comprises the first portion of the samples exceeding a magnitude, and wherein the second segmentation feature comprises the second portion of the samples being below the magnitude.

Example 13 may include the one or more computer-readable media of example 10, wherein the instructions, when executed by the device, further cause the device to perform a first decimation procedure to the first portion of the samples with the first decimation map, and perform a second decimation procedure to the second portion of the samples with the second decimation map.

Example 14 may include the one or more computer-readable media of example 13, wherein the instructions, when executed by the device, further cause the device to provide a result of the first decimation procedure to a remote device, provide a result of the second decimation procedure to the remote device, provide the first decimation map to the remote device, and provide the second decimation map to the remote device, the remote device to utilize the first decimation map with the result of the first decimation procedure and utilize the second decimation map with the result of the second decimation procedure to produce a representation of the signal.

Example 15 may include the one or more computer-readable media of example 13, wherein the instructions, when executed by the device, further cause the device to apply delta coding to a result of the first decimation procedure, and apply delta coding to a result of the second decimation procedure.

Example 16 may include the one or more computer-readable media of example 13, wherein the instructions, when executed by the device, further cause the device to apply Huffman coding to a result of the first decimation procedure, and apply Huffman coding to a result of the second decimation procedure.

Example 17 may include a method for decimating samples of a signal, comprising identifying a first portion of the samples having a first segmentation feature, identifying a second portion of the samples having a second segmentation feature, determining a first order for decimation of the first portion of the samples based on one or more approximations of the first portion of the samples and a first error threshold for the first portion of the samples, and determining a second order for decimation of the second portion of the samples based on one or more approximations of the second portion of the samples and a second error threshold for the second portion of the samples.

Example 18 may include the method of example 17, wherein the first order indicates a first number of samples to be averaged for the decimation of the first portion of the samples, and wherein the second order indicates a second number of samples to be averaged for the decimation of the second portion of the samples.

Example 19 may include the method of example 17, further comprising generating a first decimation map for the first portion of the samples based on the first order, and generating a second decimation map for the second portion of the samples based on the second order.

Example 20 may include the method of example 19, further comprising decimating the first portion of the samples via the first decimation map, wherein a result of the decimating of the first portion of the samples and the first decimation map is to be utilized for producing a first portion of a representation of the signal, and decimating the second portion of the samples via the second decimation map, wherein a result of the decimating of the second portion of the samples and the second decimation map is to be utilized for producing a second portion of the representation of the signal.

Example 21 may include a device, comprising a memory device to store a lead model and a lead measurement, a microcontroller coupled to the memory device, the microcontroller to generate a lead estimate based on the lead model and the lead measurement, determine a difference between the lead estimate and the lead measurement to produce a representation of the difference, and compress the representation of the difference to produce a lead error.

Example 22 may include the device of example 21, wherein to generate the lead estimate includes to find peaks within the lead measurement, generate a timing reference based on the peaks, and perform a reconstruction with the lead model and timing reference to produce the lead estimate.

Example 23 may include the device of example 21, wherein the lead measurement comprises a first lead measurement, and wherein the microcontroller is further to identify one or more training sequences from at least a second lead measurement, find one or more peaks within the one or more training sequences, generate a timing reference based on the one or more training sequences and the one or more peaks, and construct the lead model based on the timing reference and the at least the second lead measurement.

Example 24 may include the device of example 21, wherein to compress the representation of the difference to produce the lead error comprises includes to determine a decimation map for the representation of the difference, and decimate the representation of the difference according to the decimation map to produce the lead error.

The foregoing outlines features of one or more embodiments of the subject matter disclosed herein. These embodiments are provided to enable a person having ordinary skill in the art (PHOSITA) to better understand various aspects of the present disclosure. Certain well-understood terms, as well as underlying technologies and/or standards may be referenced without being described in detail. It is anticipated that the PHOSITA will possess or have access to background knowledge or information in those technologies and standards sufficient to practice the teachings of the present disclosure.

The PHOSITA will appreciate that they may readily use the present disclosure as a basis for designing or modifying other processes, structures, or variations for carrying out the same purposes and/or achieving the same advantages of the embodiments introduced herein. The PHOSITA will also recognize that such equivalent constructions do not depart from the spirit and scope of the present disclosure, and that they may make various changes, substitutions, and alterations herein without departing from the spirit and scope of the present disclosure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The particular embodiments of the present disclosure may readily include a system on chip (SoC) central processing unit (CPU) package. An SoC represents an integrated circuit (IC) that integrates components of a computer or other electronic system into a single chip. It may contain digital, analog, mixed-signal, and radio frequency functions: all of which may be provided on a single chip substrate. Other embodiments may include a multi-chip-module (MCM), with a plurality of chips located within a single electronic package and configured to interact closely with each other through the electronic package. Any module, function, or block element of an ASIC or SoC can be provided, where appropriate, in a reusable "black box" intellectual property (IP) block, which can be distributed separately without disclosing the logical details of the IP block. In various other embodiments, the digital signal processing functionalities may be implemented in one or more silicon cores in application-specific integrated circuits (ASICs), field-programmable gate arrays (FPGAs), and other semiconductor chips.

In some cases, the teachings of the present disclosure may be encoded into one or more tangible, non-transitory computer-readable mediums having stored thereon executable instructions that, when executed, instruct a programmable device (such as a processor or DSP) to perform the methods or functions disclosed herein. In cases where the teachings herein are embodied at least partly in a hardware device (such as an ASIC, IP block, or SoC), a non-transitory medium could include a hardware device hardware-programmed with logic to perform the methods or functions disclosed herein. The teachings could also be practiced in the form of Register Transfer Level (RTL) or other hardware description language such as VHDL or Verilog, which can be used to program a fabrication process to produce the hardware elements disclosed.

In example implementations, at least some portions of the processing activities outlined herein may also be implemented in software. In some embodiments, one or more of these features may be implemented in hardware provided external to the elements of the disclosed figures, or consolidated in any appropriate manner to achieve the intended functionality. The various components may include software (or reciprocating software) that can coordinate in order to achieve the operations as outlined herein. In still other embodiments, these elements may include any suitable algorithms, hardware, software, components, modules, interfaces, or objects that facilitate the operations thereof.

Additionally, some of the components associated with described microprocessors may be removed, or otherwise consolidated. In a general sense, the arrangements depicted in the figures may be more logical in their representations, whereas a physical architecture may include various permutations, combinations, and/or hybrids of these elements. It is imperative to note that countless possible design configurations can be used to achieve the operational objectives outlined herein. Accordingly, the associated infrastructure has a myriad of substitute arrangements, design choices, device possibilities, hardware configurations, software implementations, equipment options, etc.

Any suitably-configured processor component can execute any type of instructions associated with the data to achieve the operations detailed herein. Any processor disclosed herein could transform an element or an article (for example, data) from one state or thing to another state or thing. In another example, some activities outlined herein may be implemented with fixed logic or programmable logic (for example, software and/or computer instructions executed by a processor) and the elements identified herein could be some type of a programmable processor, programmable digital logic (for example, an FPGA, an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof. In operation, processors may store information in any suitable type of non-transitory storage medium (for example, random access memory (RAM), read only memory (ROM), FPGA, EPROM, electrically erasable programmable ROM (EEPROM), etc.), software, hardware, or in any other suitable component, device, element, or object where appropriate and based on particular needs. Further, the information being tracked, sent, received, or stored in a processor could be provided in any database, register, table, cache, queue, control list, or storage structure, based on particular needs and implementations, all of which could be referenced in any suitable timeframe. Any of the memory items discussed herein should be construed as being encompassed within the broad term 'memory.' Similarly, any of the potential processing elements, modules, and machines described herein should be construed as being encompassed within the broad term 'microprocessor' or 'processor.' Furthermore, in various embodiments, the processors, memories, network cards, buses, storage devices, related peripherals, and other hardware elements described herein may be realized by a processor, memory, and other related devices configured by software or firmware to emulate or virtualize the functions of those hardware elements.

Computer program logic implementing all or part of the functionality described herein is embodied in various forms, including, but in no way limited to, a source code form, a computer executable form, a hardware description form, and various intermediate forms (for example, mask works, or forms generated by an assembler, compiler, linker, or locator). In an example, source code includes a series of computer program instructions implemented in various programming languages, such as an object code, an assembly language, or a high-level language such as OpenCL, RTL, Verilog, VHDL, Fortran, C, C++, JAVA, or HTML for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In another example embodiment, the electrical circuits of the FIGURES may be implemented as standalone modules (e.g., a device with associated components and circuitry configured to perform a specific application or function) or implemented as plug-in modules into application-specific hardware of electronic devices.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this disclosure. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke 35 U.S.C. § 112(f) as it exists on the date of the filing hereof unless the words "means for" or "steps for" are specifically used in the particular claims; and (b) does not intend, by any statement in the disclosure, to limit this disclosure in any way that is not otherwise reflected in the appended claims.

What is claimed is:

1. A device, comprising:
a memory device to store samples of a signal; and
a microcontroller coupled to the memory device, the microcontroller to:
assign a first portion of the samples to a first segment based on a segmentation feature of the first portion of the samples;
assign a second portion of the samples to a second segment based on a segmentation feature of the second portion of the samples;
perform decimation of the first segment, wherein the decimation of the first segment utilizes a first segment order approximation for the decimation of the first segment; and
perform decimation of the second segment, wherein the decimation of the second segment utilizes a second segment order approximation for the decimation of the second segment.

2. The device of claim 1, wherein the segmentation feature of the first portion of the samples comprises values of the first portion of the samples exceeding a certain magnitude, and wherein the segmentation feature of the second portion of the samples comprises values of the second portion of the samples being below the certain magnitude.

3. The device of claim 1, wherein the first segment order approximation is determined based on an average of the first portion of the samples and a first error threshold for the first segment, and wherein the second segment order approximation is determined based on an average of the second portion of the samples and a second error threshold for the second segment.

4. The device of claim 3, wherein the first error threshold is determined based on the segmentation feature of the first portion of the samples, and wherein the second error threshold is determined based on the segmentation feature of the second portion of the samples.

5. The device of claim 4, wherein the first error threshold and the second error threshold are different.

6. The device of claim 1, wherein the first segment order approximation is of a different order from the second segment order approximation.

7. The device of claim 1, wherein the microcontroller is further to:
generate one or more approximations of the first segment;
compare one or more values of the one or more approximations of the first segment with values of the first portion of the samples to determine amounts of error for the one or more approximations of the first segment;
compare the amounts of error for the one or more approximations of the first segment with a first error threshold, wherein an order of the first segment order approximation is determined based on the comparison of the amounts of error for the one or more approximations of the first segment with the first error threshold;

generate one or more approximations of the second segment;

compare one or more values of the one or more approximations of the second segment with values of the second portion of the samples to determine amounts of error for the one or more approximations of the second segment; and compare the amounts of error for the one or more approximations of the second segment with a second error threshold, wherein an order of the second segment order approximation is determined based on the comparison of the amounts of error for the one or more approximations of the second segment with the second error threshold.

8. The device of claim 1, wherein:
to perform the decimation of the first segment includes to produce a first decimation map for the first segment based on the first segment order approximation, wherein the first decimation map is utilized for the decimation of the first segment; and
to perform the decimation of the second segment includes to produce a second decimation map for the second segment based on the second segment order approximation, wherein the second decimation map is utilized for the decimation of the second segment.

9. The device of claim 8, wherein the microcontroller is further to:
provide a result of the decimation of the first segment to a remote device;
provide the first decimation map to the remote device;
provide a result of the decimation of the second segment to the remote device; and
provide the second decimation map to the remote device, wherein the remote device is to utilize the first decimation map with the first segment and the second decimation map with the second segment to produce a representation of the signal.

10. One or more non-transitory computer-readable media having instructions stored thereon, wherein the instructions, when executed by a device, cause the device to: identify a first portion of samples of a signal, the first portion of the samples identified based on a first segmentation feature common to the first portion of the samples; identify a second portion of the samples, the second portion of the samples identified based on a second segmentation feature common to the second portion of the samples; determine a first decimation map for the first portion of the samples based on an approximation of the first portion of the samples and a first error threshold for the first portion of the samples; and determine a second decimation map for the second portion of the samples based on an approximation of the second portion of the samples and a second error threshold for the second portion of the samples.

11. The one or more non-transitory computer-readable media of claim 10, wherein: to determine the first decimation map includes to: generate one or more approximations of the first portion of the samples, wherein each of the one or more approximations of the first portion is of different order; and compare values of the one or more approximations of the first portion of the samples with the first portion of the samples to determine which of the one or more approximations of the first portion of the samples are within the first error threshold, wherein the approximation of the first portion of the samples utilized for determination of the first decimation map is included in the one or more approximations of the first portion of the samples that are within the first error threshold; and to determine the second decimation map includes to: generate one or more approximations of the second portion of the samples, wherein each of the one or more approximations of the second portion is of different order; and compare values of the one or more approximations of the second portion of the samples with the second portion of the samples to determine which of the one or more approximations of the second portion of the samples are within the second error threshold, wherein the approximation of the second portion of the samples utilized for determination of the second decimation map is included in the one or more approximations of the second portion of the samples that are within the second error threshold.

12. The one or more non-transitory computer-readable media of claim 10, wherein the first segmentation feature comprises the first portion of the samples exceeding a magnitude, and wherein the second segmentation feature comprises the second portion of the samples being below the magnitude.

13. The one or more non-transitory computer-readable media of claim 10, wherein the instructions, when executed by the device, further cause the device to: perform a first decimation procedure to the first portion of the samples with the first decimation map; and perform a second decimation procedure to the second portion of the samples with the second decimation map.

14. The one or more non-transitory computer-readable media of claim 13, wherein the instructions, when executed by the device, further cause the device to: provide a result of the first decimation procedure to a remote device; provide a result of the second decimation procedure to the remote device; provide the first decimation map to the remote device; and provide the second decimation map to the remote device, the remote device to utilize the first decimation map with the result of the first decimation procedure and utilize the second decimation map with the result of the second decimation procedure to produce a representation of the signal.

15. The one or more non-transitory computer-readable media of claim 13, wherein the instructions, when executed by the device, further cause the device to: apply delta coding to a result of the first decimation procedure; and apply delta coding to a result of the second decimation procedure.

16. The one or more non-transitory computer-readable media of claim 13, wherein the instructions, when executed by the device, further cause the device to: apply Huffman coding to a result of the first decimation procedure; and apply Huffman coding to a result of the second decimation procedure.

17. A method for decimating samples of a signal, the method comprising:
identifying a first portion of the samples based on a first segmentation feature common to the first portion of the samples;
identifying a second portion of the samples based on a second segmentation feature common to the second portion of the samples;
determining a first order for decimation of the first portion of the samples based on one or more approximations of the first portion of the samples and a first error threshold for the first portion of the samples; and
determining a second order for decimation of the second portion of the samples based on one or more approximations of the second portion of the samples and a second error threshold for the second portion of the samples.

18. The method of claim 17, wherein the first order indicates a first number of samples to be averaged for the decimation of the first portion of the samples, and wherein the second order indicates a second number of samples to be averaged for the decimation of the second portion of the samples.

19. The method of claim 17, further comprising:
generating a first decimation map for the first portion of the samples based on the first order; and
generating a second decimation map for the second portion of the samples based on the second order.

20. The method of claim 19, further comprising:
decimating the first portion of the samples via the first decimation map, wherein a result of the decimating of the first portion of the samples and the first decimation map is to be utilized for producing a first portion of a representation of the signal; and
decimating the second portion of the samples via the second decimation map, wherein a result of the decimating of the second portion of the samples and the second decimation map is to be utilized for producing a second portion of the representation of the signal.

21. The method of claim 17, wherein the first segmentation feature comprises values of the first portion of the samples exceeding a magnitude, and wherein the second segmentation feature comprises values of the second portion of the samples being below the magnitude.

22. The method of claim 17, wherein the first error threshold for the first portion of the samples is determined based on the first segmentation feature, and wherein the second error threshold for the second portion of the samples is determined based on the second segmentation feature.

* * * * *